United States Patent
Nie et al.

(10) Patent No.: US 12,208,242 B2
(45) Date of Patent: Jan. 28, 2025

(54) CLOSED-LOOP ARTIFICIAL PANCREAS SYSTEM BASED ON WEARABLE MONITORING METHOD

(71) Applicant: SHENZHEN INSTITUTES OF ADVANCED TECHNOLOGY CHINESE ACADEMY OF SCIENCES, Shenzhen (CN)

(72) Inventors: Zedong Nie, Shenzhen (CN); Jingzhen Li, Shenzhen (CN); Yuhang Liu, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 902 days.

(21) Appl. No.: 17/312,950

(22) PCT Filed: Nov. 13, 2020

(86) PCT No.: PCT/CN2020/128560
§ 371 (c)(1),
(2) Date: Jun. 11, 2021

(87) PCT Pub. No.: WO2021/232707
PCT Pub. Date: Nov. 25, 2021

(65) Prior Publication Data
US 2022/0313909 A1    Oct. 6, 2022

(30) Foreign Application Priority Data
May 19, 2020    (CN) .......................... 202010424624.1

(51) Int. Cl.
*G16H 20/17*    (2018.01)
*A61M 5/172*    (2006.01)
(Continued)

(52) U.S. Cl.
CPC .......... *A61M 5/1723* (2013.01); *G16H 20/17* (2018.01); *G16H 40/63* (2018.01); *G16H 50/20* (2018.01); *A61M 2230/201* (2013.01)

(58) Field of Classification Search
None
See application file for complete search history.

(56) References Cited

FOREIGN PATENT DOCUMENTS

WO    WO-2018111712 A1 *    6/2018    ......... A61B 5/14532

* cited by examiner

*Primary Examiner* — Karlheinz R. Skowronek
*Assistant Examiner* — Noah Andrew Auger
(74) *Attorney, Agent, or Firm* — Nitin Kaushik

(57) ABSTRACT

A closed-loop artificial pancreas system based on a wearable monitoring method is provided. The system includes: a wearable blood glucose monitoring submodule, configured to obtain a blood glucose sensing signal in a noninvasive manner by utilizing a wearable device; a diet and exercise monitoring submodule, configured to obtain diet monitoring data and exercise monitoring data which can cause variations of blood glucose concentration of a subject to be tested; a calculation control submodule, configured to obtain information related to insulin infusion by utilizing a trained deep learning model, the diet monitoring data, and the exercise monitoring data; an insulin infusion submodule, configured to automatically implement insulin infusion; and an effect assessment module, configured to assess an insulin infusion effect, and to feed an assessment result back to the calculation control submodule, such that the calculation control submodule determines whether to update the information related to insulin infusion.

7 Claims, 2 Drawing Sheets

(51) Int. Cl.
*G16H 40/63* (2018.01)
*G16H 50/20* (2018.01)

CLOSED-LOOP ARTIFICIAL PANCREAS SYSTEM BASED ON WEARABLE MONITORING METHOD

CROSS REFERENCE TO THE RELATED APPLICATIONS

This application is the national stage entry of International Application No. PCT/CN2020/128560, filed on Nov. 13, 2020, which is based upon and claims priority to Chinese Patent Application No. 202010424624.1, filed on May 19, 2020, the entire contents of which are incorporated herein by reference.

TECHNICAL FIELD

The present disclosure relates to the field of medical & healthcare technologies, and more particularly, to a closed-loop artificial pancreas system based on a wearable monitoring method.

BACKGROUND

Diabetes is a metabolic disease characterized by hyperglycemia. The occurrence of hyperglycemia is caused by insulin secretion dysfunction or impaired biological effects, or both. At present, there is no feasible radical cure for the diabetes. Diabetic patients especially Type I diabetes patients need to adjust dose of insulin in time by measuring a blood glucose concentration to control a blood glucose level and prevent or alleviate diabetes complications.

Current methods for controlling blood glucose levels include: 1) obtaining the patients' blood glucose concentration by means of a minimally invasive blood glucose meter and adjusting the dose of insulin according to the blood glucose concentration. This method requires frequent fingerpicking and blood sampling, which may cause greater pain and infection risk to the patients. Furthermore, this method cannot achieve real-time adjustment of the dose of insulin. 2) Automatically obtaining the patients' blood glucose concentration by means of an implantable continuous glucose monitoring (CGM) sensor and wearing an insulin infusion pump, wherein the insulin infusion pump can automatically adjust an insulin infusion dose according to the blood glucose concentration, such that an artificial pancreas system is formed. However, the implantable CGM sensor may cause allergies and infections to some patients, and the sensor has a shorter life span and thus needs to be replaced at regular intervals. In addition, generally only daily life conditions are considered in the existing artificial pancreas system. When the patients are eating or doing exercises, the function of the artificial pancreas system in automatically adjusting the dose of insulin is not so desirable.

The artificial pancreas system is mainly composed of a continuous blood glucose monitor, a calculation control system, and an insulin infusion pump. The continuous blood glucose monitor is configured to obtain blood glucose concentration data in real time. The calculation control system is configured to calculate and automatically adjust an insulin infusion rate in real time based on the received blood glucose concentration data, thereby ensuring accuracy of replacing the pancreatic endocrine function. In the existing technologies, the artificial pancreas system has following defects. The artificial pancreas system obtains the blood glucose concentration data by means of the implantable CGM sensor. The implanted CGM sensor may cause allergies and infections to patients, and the sensor has a shorter life span and thus needs to be replaced at regular intervals, leading to higher usage costs. Furthermore, effects of diet and exercise on variations of the blood glucose concentration are not considered in the existing artificial pancreas system, resulting in poor performance of the artificial pancreas system in the automatic insulin infusion function under the above-mentioned conditions.

SUMMARY

An objective of the present disclosure is to overcome the above defects of the existing technologies by providing a closed-loop artificial pancreas system based on a wearable monitoring method to achieve real-time and noninvasive monitoring of a blood glucose concentration and to automatically and accurately adjust an insulin infusion dose according to variations of the blood glucose concentration.

The present disclosure provides a closed-loop artificial pancreas system based on a wearable monitoring method. The system includes:
  a wearable blood glucose monitoring submodule, configured to obtain, in a noninvasive manner by utilizing a wearable device, a blood glucose sensing signal reflecting a blood glucose concentration of a subject to be tested;
  a diet and exercise monitoring submodule, configured to monitor a diet behavior and an exercise behavior of the subject to be tested to obtain diet monitoring data and exercise monitoring data causing variations of the blood glucose concentration of the subject to be tested;
  a calculation control submodule, configured to obtain information related to insulin infusion for the subject to be tested by utilizing a trained deep learning model according to the blood glucose sensing signal, the diet monitoring data, and the exercise monitoring data;
  an insulin infusion submodule, configured to automatically implement insulin infusion for the subject to be tested according to the information related to insulin infusion; and
  an effect assessment module, configured to assess an insulin infusion effect, and to feed an assessment result back to the calculation control submodule, such that the calculation control submodule determines whether to update the information related to insulin infusion.

In one embodiment, the wearable blood glucose monitoring submodule includes a low-frequency sensor, a first medium-frequency sensor, a second medium-frequency sensor, and a high-frequency sensor. The low-frequency sensor includes two receiving electrodes and two exciting electrodes. The first medium-frequency sensor and the second medium-frequency sensor each include one receiving electrode and one exciting electrode, and each of the electrodes is distributed in a manner suitable for interference elimination.

In one embodiment, an excitation source frequency of the low-frequency sensor is set as 10 Hz to 1 kHz to obtain impedance spectroscopy information characterizing the blood glucose concentration. The excitation source frequencies of the first medium-frequency sensor and the second medium-frequency sensor are set as 1 kHz to 1 GHz to obtain an S21 value characterizing the blood glucose concentration. The excitation source frequency of the high-frequency sensor is set as 1 GHz to 10 GHz to obtain an S11 value characterizing the blood glucose concentration.

In one embodiment, the calculation control submodule is configured to:

set an input matrix D expressed as below:

$$D = \begin{Bmatrix} a(t-N), a(t-N+1), a(t-N+2), a(t-N+3), \ldots, a(t) \\ b(t-N), b(t-N+1), b(t-N+2), b(t-N+3), \ldots, b(t) \\ c(t-N), c(t-N+1), c(t-N+2), c(t-N+3), \ldots, c(t) \\ d(t-N), d(t-N+1), d(t-N+2), d(t-N+3), \ldots, d(t) \\ e(t-N), e(t-N+1), e(t-N+2), e(t-N+3), \ldots, e(t) \\ f(t-N), f(t-N+1), f(t-N+2), f(t-N+3), \ldots, f(t) \\ g(t-N), g(t-N+1), g(t-N+2), g(t-N+3), \ldots, g(t) \end{Bmatrix}$$

wherein [a(t–N), a(t–N+1), a(t–N+2), a(t–N+3), ..., a(t)] represents the blood glucose sensing signal obtained by the low-frequency sensor from moment (t–N) to moment t, [b(t–N), b(t–N+1), b(t–N+2), b(t–N+3), ..., b(t)] represents the blood glucose sensing signal obtained by the first medium-frequency sensor from moment (t–N) to moment t, [c(t–N), c(t–N+1), c(t–N+2), c(t–N+3), ..., c(t)] represents the blood glucose sensing signal obtained by the second medium-frequency sensor from moment (t–N) to moment t,[d(t–N), d(t–N+1), d(t–N+2), d(t–N+3), ..., d(t)] represents the blood glucose sensing signal obtained by the high-frequency sensor from moment (t–N) to moment t, [e(t–N), e(t–N+1), e(t–N+2), e(t–N+3), ..., e(t)] represents a calorie intake rate from moment (t–N) to moment t, [f(t–N), f(t–N+1), f(t–N+2), f(t–N+3), ..., f(t)] represents an exercise type from moment (t–N) to moment t, [g(t–N), g(t–N+1), g(t–N+2), g(t–N+3), ..., g(t)] represents an exercise intensity from moment (t–N) to moment t, and N represents a total time length;

set an output matrix Y expressed as below:

$$Y = \begin{Bmatrix} y_1 \\ y_2 \\ y_3 \end{Bmatrix}$$

wherein $y_1$ represents an insulin infusion mode, $y_2$ represents duration time of each insulin infusion, and $y_3$ represents an insulin infusion rate; and obtain information related to insulin infusion for the subject to be tested according to a mapping relationship Y=M×D between the input matrix D and the output matrix Y.

In one embodiment, a mapping matrix M is obtained by pre-training a long short-term memory network (LSTM), wherein the long short-term memory network adopts a stack architecture and includes superposition of a plurality of LSTM layers and superposition of a plurality of Dense layers in sequence.

In one embodiment, the insulin infusion submodule is configured to drive an insulin infusion pump by means of a micromotor, and to monitor an infusion process based on gravity sensing and near infrared monitoring. The insulin infusion submodule is provided with a human body communication transmission interface to directly control the insulin infusion pump.

In one embodiment, the effect assessment submodule is configured to:

determine an input factor U={$u_1,u_2,u_3,u_4$}, the input factor U representing an expected blood glucose value U={$u_1,u_2,u_3,u_4$} of the subject to be tested after insulin infusion, wherein $u_1$ represents the expected blood glucose value at a moment t, $u_2$ represents an expected fluctuation range of blood glucose, $u_3$ represents an expected variation coefficient of blood glucose, and $u_4$ represents an expected mean value of blood glucose;

determine an output factor V={$v_1,v_2,v_3,v_4$}, wherein $v_1$ represents a true blood glucose value at a moment t, $v_2$ represents a true fluctuation range of blood glucose, $v_3$ represents a true variation coefficient of blood glucose, and $v_4$ represents a true mean value of blood glucose;

establish an assessment matrix from the input factor to the output factor to obtain a mapping matrix from U→F (V); and assess validity of the currently adopted information related to insulin infusion according to the mapping matrix obtained.

In one embodiment, the diet monitoring data include a calorie intake rate and total duration in a diet process, and the diet monitoring data are obtained by analyzing the diet behavior of the subject to be tested, wherein the diet behavior may be automatically recorded by a wearable camera device.

In one embodiment, the obtaining the diet monitoring data includes:

obtaining image information of the subject to be tested by means of the wearable camera device at a preset frequency, and uploading the image information to a cloud platform;

recognizing and parsing each frame image on the cloud platform by means of a convolutional neural network, and storing the frame image and recognizing a type of food in the image when it is recognized that the subject to be tested is eating to calculate total calories; and automatically analyzing the calorie intake rate and the total duration of the subject to be tested in the diet process according to variation of the each frame image.

In one embodiment, the exercise monitoring data include an exercise type and an exercise intensity. The exercise monitoring data are various types of sensing signals of velocities, slopes, impacts, vibrations and rotations on planes x, y and z, wherein the various types of sensing signals may be synchronous captured by a wearable three-axis motion sensor. Next, the exercise type and the exercise intensity are recognized by means of the deep learning model.

Compared with the existing technologies, advantages of the present disclosure are as below. Real-time and noninvasive monitoring of a blood glucose concentration is achieved based on a wearable monitoring method, and based on effects of diets and exercises on variations of the blood glucose concentration, an insulin infusion dose is automatically adjusted according to the variations of the blood glucose concentration, such that a closed-loop artificial pancreas system is formed.

Other features and advantages of the present disclosure will become apparent from the following detailed description of exemplary embodiments of the present disclosure with reference to accompanying drawings.

BRIEF DESCRIPTION OF THE DRAWINGS

The accompanying drawings herein are incorporated in and constitute a part of this specification, illustrate embodiments of the present disclosure and, together with the specification, serve to explain the principles of the present disclosure.

DETAILED DESCRIPTION

Figure 1:
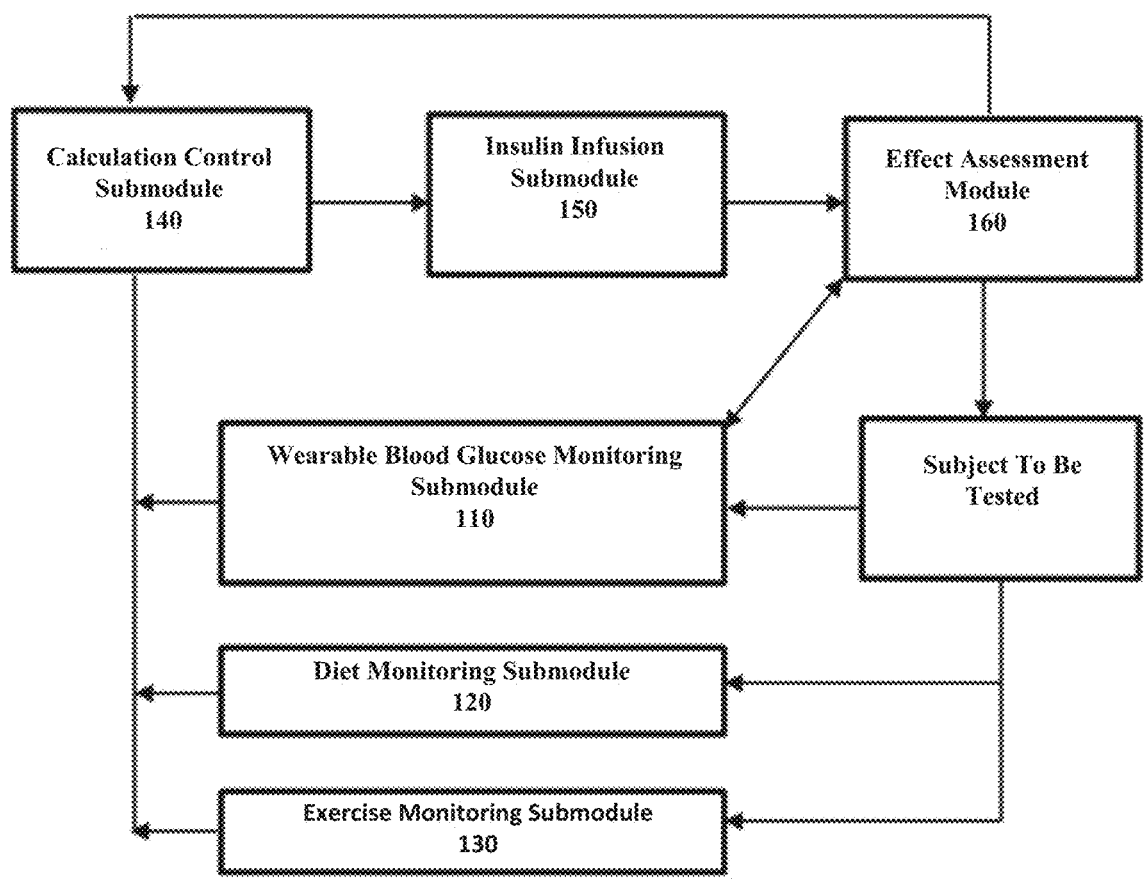
FIG. 1 is a schematic diagram of a closed-loop artificial pancreas system based on a wearable monitoring method according to one embodiment of the present disclosure.

Various exemplary embodiments of the present disclosure will now be described in detail with reference to the accompanying drawings. It is to be noted that the relative arrangement, numerical expressions, and numerical values of the components and steps set forth in these embodiments do not limit the scope of the present disclosure unless otherwise specifically stated.

The following description of at least one exemplary embodiment is actually merely illustrative, and in no way serves as any limitation on the present disclosure and application or use thereof.

Technologies, methods and equipment known to those of ordinary skill in the related art may not be discussed in detail, but where appropriate, the technologies, methods and equipment should be considered as part of the specification.

In all examples shown and discussed herein, any specific values should be interpreted as merely exemplary and not limiting. Therefore, other examples of the exemplary embodiment may have different values.

It is to be noted that similar reference numerals and letters indicate similar items in the following accompanying drawings. Therefore, once an item is defined in one drawing, there is no need to discuss this item further in subsequent drawings.

With reference to FIG. 1, a closed-loop artificial pancreas system based on a wearable monitoring method provided by embodiments of the present disclosure includes a wearable blood glucose monitoring submodule 110, a diet monitoring submodule 120, an exercise monitoring submodule 130, a calculation control submodule 140, an insulin infusion submodule 150, and an effect assessment module 160.

Figure 2:
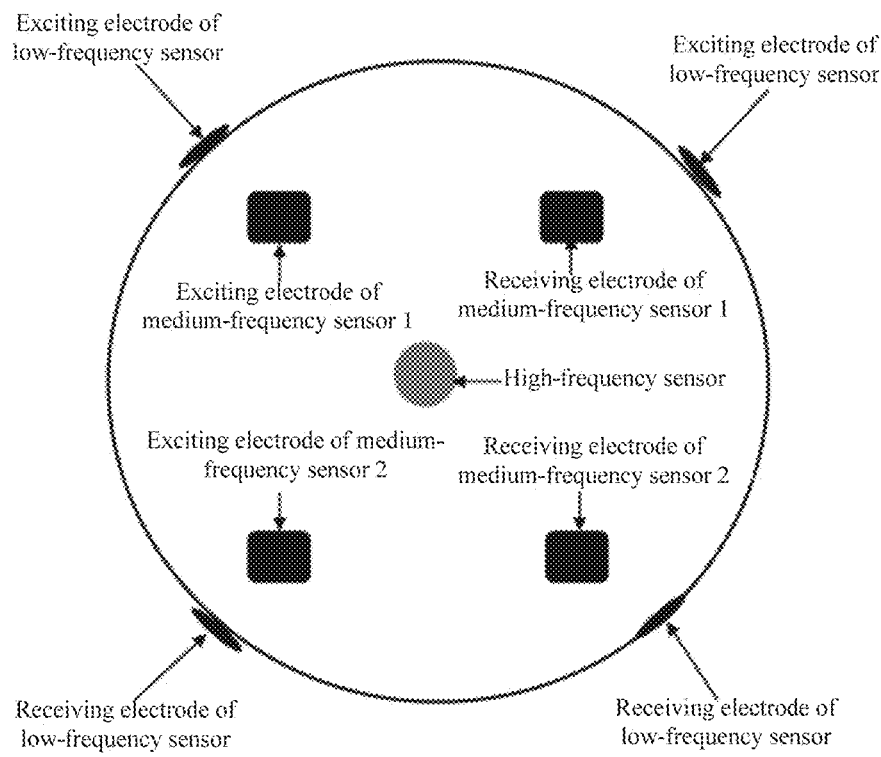
FIG. 2 is a schematic diagram of a wearable monitoring submodule according to one embodiment of the present disclosure.

The wearable blood glucose monitoring submodule 110 is configured to continuously and noninvasively obtain blood glucose sensing data based on wearable technologies. For example, as a wearable device fit for being worn on a wrist or an upper arm, this submodule includes one set of low-frequency sensors, two sets of medium-frequency sensors (i.e., medium-frequency sensor 1 and medium-frequency sensor 2), and one set of high-frequency sensors. In a blood glucose monitoring process, the four sets of sensors work synchronously. To avoid mutual interferences between different sensors, distribution positions of each set of sensors in the wearable device are as shown in FIG. 2. In one embodiment, as a four-electrode sensor, the low-frequency sensor includes two receiving electrodes and two exciting electrodes, and an excitation source frequency of the low-frequency sensor is 10 Hz to 1 kHz. Monitoring of the blood glucose concentration is implemented by obtaining impedance spectroscopy information by means of the receiving electrodes and by analyzing relevance between the impedance spectroscopy information and the blood glucose concentration. As a two-electrode sensor, the medium-frequency sensor includes one exciting electrode and one receiving electrode, and an excitation source frequency of the medium-frequency sensor is 1 kHz to 1 GHz. Monitoring of the blood glucose concentration is implemented by obtaining an S21 value by means of the receiving electrode and by analyzing a relevance between the S21 value and the blood glucose concentration. An excitation source frequency of the medium-frequency sensor is 1 GHz to 10 GHz. Monitoring of the blood glucose concentration is implemented by measuring an S11 value of the sensor and by analyzing relevance between the S11 value and the blood glucose concentration.

It is to be understood that monitoring of the blood glucose concentration also may be implemented by means of more or fewer sets of sensors, and distribution of electrodes of the sensors may be in various forms. For clarity, principles and specific embodiments are illustrated by taking four sets of sensors as an example herein.

The diet monitoring submodule 120 is configured to monitor a state or an action behavior of the subject to be tested to obtain related data that may affect the blood glucose concentration. For example, this submodule can automatically record diet information of the subject to be tested by means of a wearable camera device. First, the subject to be tested wears a wearable camera device, such as smart glasses with camera function, etc. This device automatically obtains image information of the subject to be tested at a frequency of once per minute and uploads the image information to a cloud platform. On the cloud platform, each frame image is recognized and parsed by means of a convolutional neural network. When it is recognized that the subject to be tested is eating or drinking, this frame image is stored, and by processing (such as image segmentation and feature extraction) this frame image based on the information of this frame image, food in the image is recognized based on an image recognition algorithm to analyze a type of the food in the image to calculate total calories. Moreover, according to variations of each frame image, information such as a calorie intake rate and total duration in a diet process may be automatically analyzed for the subject to be tested.

The exercise monitoring submodule 130 is configured to obtain exercise information of the subject to be tested. For example, the subject to be tested wears a wearable three-axis motion sensor. Different types of sensing signals of velocities, slopes, impacts, vibrations and rotations on planes x, y and z are synchronously obtained by means of the motion sensor. Variation features of the sensing signals on the planes x, y and z are synthetically considered, and a current exercise type (such as sitting still, running, and playing basketball) and a current exercise intensity of the subject to be tested are recognized based on an intelligent recognition algorithm for deep learning. For example, the exercise intensity is classified into ten grades from Grade 1 to Grade 10, which are respectively corresponding to different intensities from weak to strong.

The calculation control submodule 140 is configured to train the above data using a deep learning algorithm according to the blood glucose sensing data, the diet monitoring data, and the exercise monitoring data. Output results include an insulin infusion mode, an insulin infusion speed, and insulin infusion duration.

In one embodiment, concrete implementation procedures of the calculation control submodule 140 are as below (taking four sets of sensors as an example).

An input matrix of the calculation control submodule is set as D, and the input matrix may be expressed as Formula (1), wherein [a(t−N), a(t−N+1), a(t−N+2), a(t−N+3), . . . , a(t)] represents the blood glucose sensing signal obtained by the low-frequency sensor from moment (t−N) to moment t, [b(t−N), b(t−N+1), b(t−N+2), b(t−N+3), . . . , b(t)] represents the blood glucose sensing signal obtained by the medium-frequency sensor 1 from moment (t–N) to moment t, [c(t–N), c(t–N+1), c(t–N+2), c(t–N+3), . . . , c(t)] represents the blood glucose sensing signal obtained by the medium-frequency sensor 2 from moment (t–N) to moment t, [d(t–N), d(t–N+1), d(t–N+2), d(t–N+3), . . . , d(t)] represents the blood glucose sensing signal obtained by the high-frequency sensor from moment (t–N) to moment t, [e(t–N), e(t–N+1), e(t–N+2), e(t–N+3), . . . , e(t)] represents a calorie intake rate from moment (t–N) to moment t, and [f(t–N), f(t–N+1), f(t–N+2), f(t–N+3), . . . , f(t)] represents an exercise type from moment (t–N) to moment t. For ease of analysis, the exercise type of the subject to be tested is digitally processed. That is, sitting still is represented by 1, running is represented by 2, playing basketball is represented by 3, and playing football is represented by 4, etc. [g(t–N), g(t–N+1), g(t–N+2), g(t–N+3), . . . , g(t)] represents an exercise intensity from moment (t–N) to moment t. N represents a total time length. Time is measured in minutes herein. Therefore, for example, N=120 represents that the data time length is 120 minutes.

$$D = \begin{Bmatrix} a(t-N), a(t-N+1), a(t-N+2), a(t-N+3), \ldots, a(t) \\ b(t-N), b(t-N+1), b(t-N+2), b(t-N+3), \ldots, b(t) \\ c(t-N), c(t-N+1), c(t-N+2), c(t-N+3), \ldots, c(t) \\ d(t-N), d(t-N+1), d(t-N+2), d(t-N+3), \ldots, d(t) \\ e(t-N), e(t-N+1), e(t-N+2), e(t-N+3), \ldots, e(t) \\ f(t-N), f(t-N+1), f(t-N+2), f(t-N+3), \ldots, f(t) \\ g(t-N), g(t-N+1), g(t-N+2), g(t-N+3), \ldots, g(t) \end{Bmatrix} \quad (1)$$

An output matrix of the calculation control submodule is set as Y, and this output matrix may be expressed as Formula (2), wherein $y_1$ represents an insulin infusion mode. For example, $y_1=0$ represents a continuous insulin infusion, and $y_1 \neq 0$ represents an insulin infusion at intervals, and the larger the value of $y_1$ is, the longer the infusion interval time is. $y_2$ represents duration time of each insulin infusion, and $y_3$ represents an insulin infusion rate.

$$Y = \begin{Bmatrix} y_1 \\ y_2 \\ y_3 \end{Bmatrix} \quad (2)$$

Figure 3:
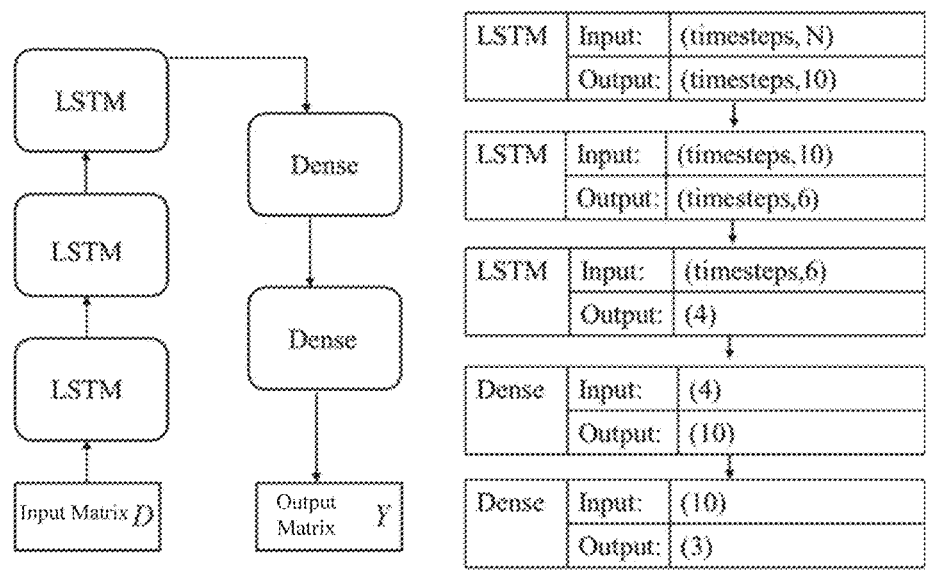
FIG. 3 is a block diagram showing implementation based on an LSTM according to one embodiment of the present disclosure; and In the figures, Input-input; Output-output; timesteps-timesteps; and Dense-fully connected layer.

A mapping relationship between the input matrix D and the output matrix Y may be expressed as Formula (3), wherein M represents a mapping matrix, and a size of the mapping matrix M may be determined based on a long short-term memory network (LSTM) algorithm. As shown in FIG. 3, the LSTM adopts a stack architecture including superposition of three LSTM layers and superposition of two Dense layers. Input and output dimensions of each layers are as shown in FIG. 3, wherein N represents a total time length, and timesteps represent timesteps in the LSTM network.

$$Y = M \times D \quad (3)$$

In another embodiment, the calculation control submodule 140 may also determine the information related to insulin infusion by employing other time recurrent neural networks such as a gated recurrent unit (GRU), etc.

The insulin infusion submodule 150 is configured to automatically implement insulin infusion for the subject to be tested according to the output result of the calculation control submodule 140. To achieve precise insulin infusion, in one embodiment, an insulin infusion pump is driven by means of a micromotor, and meanwhile an infusion process is monitored based on gravity sensing and near infrared monitoring. An alarm signal will be issued immediately if something unexpected happens. In addition, a human body communication transmission interface is reserved for the insulin infusion submodule 150 to provide an additional link for the insulin infusion pump, such that the insulin infusion pump can be directly controlled by means of the human body communication transmission interface when necessary.

The effect assessment module 160 is configured to assess an insulin infusion effect, and to feed an assessment result back to the calculation control submodule 140.

In one embodiment, implementation procedures of the effect assessment submodule 160 are as below.

An input factor is determined, the input factor U represents an expected blood glucose value $U=\{u_1,u_2,u_3,u_4\}$ of the subject to be tested after insulin infusion, wherein $u_1$ represents the expected blood glucose value at a moment t, $u_2$ represents an expected fluctuation range of blood glucose, $u_3$ represents an expected variation coefficient of blood glucose, and $u_4$ represents an expected mean value of blood glucose.

An output factor is determined, the output factor is represented by $V=\{v_1,v_2,v_3,v_4\}$, wherein $v_1$ represents a true blood glucose value at a moment t, $v_2$ represents a true fluctuation range of blood glucose, $v_3$ represents a true variation coefficient of blood glucose, and $v_4$ represents a true mean value of blood glucose. A method for determining sizes of values $v_1$, $v_2$, $v_3$ and $v_4$ is as below. Four sets of blood glucose sensing signals (low-frequency sensor, medium-frequency sensor 1, medium-frequency sensor 2, and high-frequency sensor) are obtained by means of the wearable blood glucose monitoring submodule, and the blood glucose sensing signals are converted to blood glucose concentration values according to a fitting function for the sensing signals and the blood glucose concentration values. The values of $v_1$, $v_2$, $v_3$ and $v_4$ may be obtained by calculating a mean value for the above four sets of sensors.

An assessment matrix from the input factor to the output factor is established to obtain a mapping matrix from $U \rightarrow F(V)$.

$$M_1: U \rightarrow F(V) \; \forall u_i \in U$$

The assessment matrix $M_1$ may be obtained according to the deduced mapping matrix.

$$M_1 = \begin{pmatrix} r_{11} & r_{12} & \ldots & r_{1m} \\ r_{21} & r_{22} & \ldots & r_{2m} \\ \ldots & \ldots & \ldots & \ldots \\ r_{n1} & r_{n2} & \ldots & r_{nm} \end{pmatrix}$$

For example, if the assessment result is $$\sum_{j=1}^{m} r_i \neq i,$$

normalization processing is performed on the assessment result. Finally, according to a maximum membership rule, an item corresponding to the maximum r is the assessment result. If the value of $r_i$ is less than 10%, this indicates that an insulin infusion scheme is reasonable. Otherwise, the insulin infusion scheme is recalculated based on the LSTM algorithm.

In conclusion, the closed-loop artificial pancreas system based on the wearable monitoring method provided by the present disclosure can carry out noninvasive monitoring of a blood glucose concentration by means of a wearable device. Furthermore, based on effects of diets and exercises on variations of the blood glucose concentration, an insulin infusion dose is adjusted according to the variations of the blood glucose concentration, and insulin infusion information is automatically adjusted according to an insulin infusion effect, such that a closed-loop artificial pancreas system is formed. It has been verified that the system provided by the present disclosure can achieve good blood glucose control under different conditions and can avoid the occurrence of hyperglycemic and hypoglycemic events.

The present disclosure may be a system, a method, and/or a computer program product. The computer program product may include a computer readable storage medium having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. More specific examples (a non-exhaustive list) of the computer readable storage medium include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. The computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical fiber transmission, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In a scenario involved with the remote computer, the remote computer may be coupled to the user's computer through any type of network, including a local area network (LAN) or a wide area network (WAN), or may be coupled to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described with reference to flowcharts and/or block diagrams according to the method, apparatus (system) and a computer program product of the embodiments of the present disclosure. It is to be understood that each block of the flowcharts and/or block diagrams, and combinations of blocks in the flowcharts and/or block diagrams, can be implemented by computer readable program instructions.

These computer readable program instructions may be provided to a processor of a general purpose computer, special purpose computer, or other programmable data processing apparatus to produce a machine, such that these instructions, which execute via the processor of the computer or other programmable data processing apparatus, create means for implementing the functions/acts specified in one or more blocks in the flowcharts and/or block diagrams. These computer readable program instructions may also be stored in a computer readable storage medium that can direct a computer, a programmable data processing apparatus, and/or other devices to function in a particular manner, such that the computer readable medium having instructions stored therein includes an article of manufacture including instructions which implement aspects of the function/act specified in one or more blocks in the flowcharts and/or block diagrams.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in one or more blocks in the flowcharts and/or block diagrams.

The flowcharts and block diagrams in the accompanying drawings illustrate architectures, functions and operations of possible implementations of systems, methods, and computer program products according to a plurality of embodiments of the present disclosure. In this regard, each block in the flowcharts or block diagrams may represent a module, a program segment, or a portion of instructions, which includes one or more executable instructions for implementing the specified logical function(s). In some alternative implementations, the functions denoted by the blocks may occur in a sequence different from the sequences shown in the accompanying drawings. For example, two blocks shown in succession may, in fact, be executed substantially concurrently, or the blocks may sometimes be executed in a reverse sequence, depending upon the functions involved. It is also to be noted that each block in the block diagrams and/or flowcharts and/or a combination of the blocks in the block diagrams and/or flowcharts may be implemented by a special-purpose hardware-based system executing specific functions or acts, or by a combination of a special-purpose hardware and computer instructions. It is well known to those skilled in the art that implementations by means of hardware, implementations by means of software and implementations by means of software in combination with hardware are equivalent.

The descriptions of the various embodiments of the present disclosure have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein. The scope of the present disclosure is limited by the appended claims.

What is claimed is:

1. A closed-loop artificial pancreas system based on a wearable monitoring method, comprising:

a wearable blood glucose monitoring submodule, configured to obtain, in a noninvasive manner by utilizing a wearable device, a blood glucose sensing signal reflecting a blood glucose concentration of a subject to be tested;

a diet and exercise monitoring submodule, configured to monitor a diet behavior and an exercise behavior of the subject to be tested to obtain diet monitoring data and exercise monitoring data causing variations of the blood glucose concentration of the subject to be tested;

a calculation control submodule, configured to obtain information related to insulin infusion for the subject to be tested by utilizing a trained deep learning model according to the blood glucose sensing signal, the diet monitoring data, and the exercise monitoring data;

an insulin infusion submodule, configured to automatically implement insulin infusion for the subject to be tested according to the information related to insulin infusion; and an effect assessment submodule, configured to assess an insulin infusion effect, and to feed an assessment result back to the calculation control submodule, such that the calculation control submodule determines whether to update the information related to insulin infusion;

wherein the wearable blood glucose monitoring submodule comprises a low-frequency sensor, a first medium-frequency sensor, a second medium-frequency sensor, and a high-frequency sensor; the low-frequency sensor comprises two receiving electrodes and two exciting electrodes, the first medium-frequency sensor and the second medium-frequency sensor each comprise a receiving electrode and an exciting electrode, and each of the electrodes being distributed in a manner suitable for interference elimination;

wherein the calculation control submodule is configured to:

set an input matrix D expressed as below:

$$D = \begin{Bmatrix} a(t-N), a(t-N+1), a(t-N+2), a(t-N+3), \ldots, a(t) \\ b(t-N), b(t-N+1), b(t-N+2), b(t-N+3), \ldots, b(t) \\ c(t-N), c(t-N+1), c(t-N+2), c(t-N+3), \ldots, c(t) \\ d(t-N), d(t-N+1), d(t-N+2), d(t-N+3), \ldots, d(t) \\ e(t-N), e(t-N+1), e(t-N+2), e(t-N+3), \ldots, e(t) \\ f(t-N), f(t-N+1), f(t-N+2), f(t-N+3), \ldots, f(t) \\ g(t-N), g(t-N+1), g(t-N+2), g(t-N+3), \ldots, g(t) \end{Bmatrix}$$

wherein [a(t−N), a(t−N+1), a(t−N+2), a(t−N+3), . . . , a(t)] represents the blood glucose sensing signal obtained by the low-frequency sensor from moment (t−N) to moment t, [b(t−N), b(t−N+1), b(t−N+2), b(t−N+3), . . . , b(t)] represents the blood glucose sensing signal obtained by the first medium-frequency sensor from moment (t−N) to moment t, [c(t−N), c(t−N+1), c(t−N+2), c(t−N+3), . . . , c(t)] represents the blood glucose sensing signal obtained by the second medium-frequency sensor from moment (t−N) to moment t, [d(t−N), d(t−N+1), d(t−N+2), d(t−N+3), . . . , d(t)] represents the blood glucose sensing signal obtained by the high-frequency sensor from moment (t−N) to moment t, [e(t−N), e(t−N+1), e(t−N+2), e(t−N+3), . . . , e(t)] represents a calorie intake rate from moment (t−N) to moment t, [f(t−N), f(t−N+1), f(t−N+2), f (t−N+3), . . . , f(t)] represents an exercise type from moment (t−N) to moment t, [g(t−N), g(t−N+1), g(t−N+2), g(t−N+3), . . . , g(t)] represents an exercise intensity from moment (t−N) to moment t, and N represents a total time length;

set an output matrix Y expressed as below:

$$Y = \begin{Bmatrix} y_1 \\ y_2 \\ y_3 \end{Bmatrix}$$

wherein $y_1$ represents an insulin infusion mode, $y_2$ represents duration time of each insulin infusion, and $y_3$ represents an insulin infusion rate; and obtain information related to insulin infusion for the subject to be tested according to a mapping relationship Y=M×D between the input matrix D and the output matrix Y, wherein M is a mapping matrix;

wherein the effect assessment submodule is configured to:

determine an input factor U={$u_1, u_2, u_3, u_4$}, the input factor U representing an expected blood glucose value U={$u_1, u_2, u_3, u_4$} of the subject to be tested after insulin infusion, wherein $u_1$ represents the expected blood glucose value at a moment t, $u_2$ represents an expected fluctuation range of blood glucose, $u_3$ represents an expected variation coefficient of blood glucose, and $u_4$ represents an expected mean value of blood glucose;

determine an output factor V={$v_1, v_2, v_3, v_4$}, wherein $v_1$ represents a true blood glucose value at a moment t, $v_2$ represents a true fluctuation range of blood glucose, $v_3$ represents a true variation coefficient of blood glucose, and $v_4$ represents a true mean value of blood glucose;

establish an assessment matrix from the input factor to the output factor to obtain a mapping matrix from U→F (V); and assess validity of the currently adopted information related to insulin infusion according to the mapping matrix obtained.

2. The closed-loop artificial pancreas system according to claim 1, wherein an excitation source frequency of the low-frequency sensor is set as 10 Hz to 1 kHz to obtain impedance spectroscopy information characterizing the blood glucose concentration; the excitation source frequencies of the first medium-frequency sensor and the second medium-frequency sensor are set as 1 kHz to 1 GHz to obtain an S21 value characterizing the blood glucose concentration; and an excitation source frequency of the high-frequency sensor is set as 1 GHz to 10 GHz to obtain an S11 value characterizing the blood glucose concentration.

3. The closed-loop artificial pancreas system according to claim 1, wherein the mapping matrix M is obtained by pre-training a long short-term memory network (LSTM), the LSTM adopts a stack architecture and comprises superposition of a plurality of LSTM layers and superposition of a plurality of Dense layers in sequence.

4. The closed-loop artificial pancreas system according to claim 1, wherein the insulin infusion submodule is configured to drive an insulin infusion pump by means of a micromotor, and to monitor an infusion process based on gravity sensing and near infrared monitoring; and the insulin infusion submodule is provided with a human body communication transmission interface to directly control the insulin infusion pump.

5. The closed-loop artificial pancreas system according to claim 1, wherein the diet monitoring data comprises a calorie intake rate and total duration time in a diet process, and the diet monitoring data are obtained by analyzing the diet behavior of the subject to be tested, the diet behavior being automatically recorded by a wearable camera device.

6. The closed-loop artificial pancreas system according to claim 5, wherein the obtaining the diet monitoring data comprises:
  obtaining image information of the subject to be tested by the wearable camera device at a preset frequency, and uploading the image information to a cloud platform;
  recognizing and parsing each frame image on the cloud platform by a convolutional neural network, and storing the each frame image and recognizing a type of food in the each frame image when recognizing that the subject to be tested is eating to calculate total calories; and
  automatically analyzing the calorie intake rate and the total duration time of the subject to be tested in the diet process according to variation of the each frame image.

7. The closed-loop artificial pancreas system according to claim 1, wherein the exercise monitoring data comprise an exercise type and an exercise intensity, the exercise monitoring data being various types of sensing signals of velocities, slopes, impacts, vibrations and rotations on planes x, y and z, the various types of sensing signals being synchronously captured by a wearable three-axis motion sensor, and then the exercise type and the exercise intensity being recognized by means of the deep learning model.

* * * * *